United States Patent [19]

Turner et al.

[11] 4,051,263
[45] Sept. 27, 1977

[54] DERIVATIVES OF 1,2-DIPHENYL-ETHANE

[75] Inventors: John Cameron Turner, West Wickham; Rosalind Po-Kuen Chan, London, both of England

[73] Assignee: Biorex Laboratories Limited, London, England

[21] Appl. No.: 563,119

[22] Filed: Mar. 27, 1975

Related U.S. Application Data

[63] Continuation-in-part of Ser. No. 116,274, Feb. 17, 1971, abandoned.

[30] Foreign Application Priority Data

Mar. 16, 1970  United Kingdom ............... 12554/70

[51] Int. Cl.² .................... A61K 31/055; C07C 39/16; C07C 39/24
[52] U.S. Cl. .............................. 424/347; 260/619 R
[58] Field of Search .......... 260/619 R, 619 B, 623 R, 260/619 A, 619; 424/347

[56] References Cited

U.S. PATENT DOCUMENTS

| 2,502,325 | 3/1950 | Kaiser et al. | 260/613 |
| 2,568,809 | 9/1951 | Kaiser | 260/619 B |
| 3,499,763 | 3/1970 | Clecak et al. | 260/619 B |

FOREIGN PATENT DOCUMENTS 37-2617  5/1962  Japan .................................. 260/619

*Primary Examiner*—James O. Thomas, Jr.
*Assistant Examiner*—W. B. Lone
*Attorney, Agent, or Firm*—Wenderoth, Lind & Ponack

[57] ABSTRACT

There is provided a new derivative of 1,2-diphenyl-ethane of the formula:-

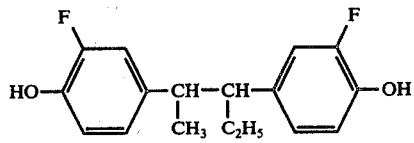

This new compound has been found to be very useful for the treatment of hypertrophied conditions of the prostate.

3 Claims, No Drawings

DERIVATIVES OF 1,2-DIPHENYL-ETHANE

CROSS-REFERENCE TO RELATED APPLICATION

This is a continuation-in-part of Ser. No. 116,274 filed Feb. 17, 1971, now abandoned.

BACKGROUND OF THE INVENTION

It is known that hexoestrol and diethylstilboestrol, as well as certain esters and mono- and diethers thereof, have been used for the treatment of diseases of the prostate.

We have now found a new compound with a structure similar to that of hexostrol and of diethylstilboestrol which is useful for the treatment of hypertrophied conditions of the prostate.

SUMMARY OF THE INVENTION

The new derivative of 1,2-diphenyl-ethane according to the present invention is a compound of the formula:

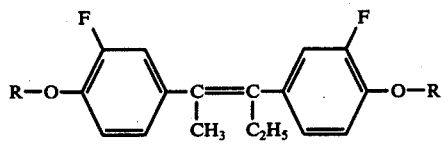

(I)

The new compound of the present invention can be prepared by reacting an ether of the general formula:

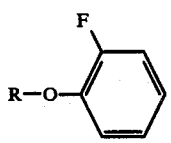

(II)

wherein R is an alkyl radical containing up to 6 carbon atoms, with a halo-ketone of the general formula:

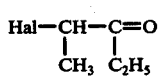

(III)

wherein Hal is a halogen atom, preferably a chlorine atom, to give an unsaturated diether of the general formula:

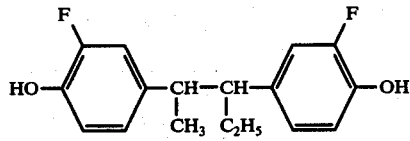

(IV)

wherein R has the same meaning as above, which is then hydrogenated to give the corresponding saturated diether of the general formula:

(V)

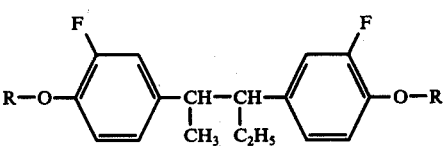

wherein R has the same meaning as above, whereafter this compound is dealkylated to give the corresponding dihydroxy compound (I).

According to another method of preparation, an ether of general formula (II) is reacted with a secondary alcohol of the general formula:

(VI)

wherein Hal has the same meaning as above, to give a diether of the general formula:

(VII)

wherein R has the same meaning as above, whereafter, if desired, this compound can then be dealkylated to give the corresponding dihydroxy compound (I).

The advantage of this method is that it renders the hydrogenation step unnecessary.

The condensation of compounds (II) and (III) is preferably carried out in the presence of concentrated sulphuric acid or of anhydrous aluminium chloride at a reduced temperature, for example, at a temperature of −25° C. to 0° C., whereas the condensation of compounds (II) and (VI) is preferably carried out in the presence of anhydrous aluminium chloride at ambient temperature or at a slightly elevated temperature, for example up to about 40° C.

The hydrogenation of the unsaturated diethers (IV) is preferably carried out catalytically in glacial acetic acid in the presence of a palladium or platinum catalyst.

The dealkylation of the products obtained can be carried out, for example, by the action of hydrobromic acid in acetic acid.

We have also found that the compound (I) according to the present invention can sometimes be difficult to purify by recrystallisation. This problem can readily be overcome by etherification of the compound (I) with a benzyl halide. The dibenzyl ether thus obtained can be readily recrystallised. The dienzyl ether purified in this manner is subsequently readily reconverted into the compound (I) by hydrogenolysis, for example, by dissolving the dibenzyl ether in glacial acetic acid and shaking up the solution with hydrogen in the presence of an appropriate catalyst, such as palladium-charcoal or platinum-oxide.

The following Examples are given for the purpose of illustrating the present invention:

EXAMPLE 1

A mixture of 100 g. redistilled 2-fluoroanisole and 50 g. 3-chloropentan-1-one (b.p. 134° – 137° C.) was cooled to −20° C. and 125 ml. concentrated sulphuric acid were added thereto dropwise, while stirring, over the course of 2 hours. After further stirring the reaction mixture for 6 hours, it was poured into ice-water. This was then extracted with diethyl ether, the ethereal extract was dried and the ether distilled off, whereafter the oily residue was heated for 2 hours at 235° - 240° C. and 15 mm.Hg. and any distillate obtained was discarded. The residue was then distilled at 160° - 170° C./0.03 mm.Hg. to give a major fraction of 20 g. of an oil which could not be crystallised. This oil was then dissolved in 150 ml. glacial acetic acid and shaken in an atmosphere of hydrogen in the presence of 1.2 g. palladium-charcoal (10%) until the uptake of hydrogen ceased. The reaction mixture was then filtered and evaporated to give about 20 g. of a mixture of threo- and erythro-3,3'-difluoro-4,4'-dimethoxy-α-ethyl-α'-dibenzyl. After crystallisation of this mixture from methanol, the erythro compound was obtained which had a melting point of 106° - 107° C.

EXAMPLE 2

A solution of 7.5 g. erythro-3,3'-difluro-4,4'-dimethoxy-α-ethyl-α'-methyl-dibenzyl (see Example 1) in 70 ml. glacial acetic acid and 40 ml. hydrobromic acid was heated under reflux in an atmosphere of nitrogen for 6.5 hours. After cooling, the reaction mixture was poured on to ice and extracted with ether. The ethereal extracts were washed with water and extracted with 2N sodium hydroxide solution. The alkaline extract was acidified and extracted with ether. Evaporation of the ethereal extract gave 6 g. of a yellowish solid which was dissolved in benzene and passed through a column containing 50 g. of silica gel. Concentration of the eluate resulted in the deposition of erythro-3,3'-difluoro-4,4'-dihydroxy-α-ethyl-α'-methyl-dibenzyl, which had a melting point of 152° - 153° C.

EXAMPLE 3

26 g. aluminium chloride were added, in the course of 1 hour, to a stirred mixture of 26 g. o-fluoroanisole and 12.5 g. 3chloropentanol in an atmosphere of nitrogen. The reaction mixture was warmed to 35° C. for 60 hours and then poured into ice water. The reaction mixture was extracted with ether and then shaken up with an aqueous solution of sodium hydroxide to remove undesired acidic phenolic material. The remaining ethereal phase was dried and evaporated to give a neutral material which was fractionally distilled. The fraction boiling at 165° - 175° C./0.2 mm.Hg. (10 g.) was recrystallised from methanol to give 1.3 g. erythro-3,3'-difluoro-4,4'-dimethoxy-α-ethyl-α'-methyl-dibenzyl, which had a melting point of 106° - 107° C. and was identical with the product of Example 1.

This dimethoxy compound was demethylated by heating in a mixture of 25 ml. glacial acetic acid and 10 ml. hydrobromic acid under an atmosphere of nitrogen at 140° C. for 5 hours. Thereafter, the solution was cooled and diluted with water. There was thus obtained 1.05 g. erythro-3,3'-difluoro-4,4'-dihydroxy-α-ethyl-α'-methyl-dibenzyl which, after recrystallisation from benzene, had a melting point of 152° - 153° C. and was identical with the product of Example 2.

The non-crystalline mother liquor was demethylated in a similar manner. The 7.5 g. of product obtained were combined with the phenolic fraction (6 g.; b.p. 180° - 190° C./0.02 mm.Hg.) and mixed with 13 g. benzyl chloride in a solution of 4 g. sodium hydroxide in 100 ml. alchohol. The reaction mixture was boiled under reflux for 2 hours and then cooled and diluted with water. There was obtained 1.9 g. of a precipitate of erythro-3,3'-difluoro-4,4'-dibenzyloxy-α-ethyl-α'-methyl-dibenzyl which, after rcrystallisation from benzene/petroleum ether, had a melting point of 131° - 132.5° C. This compound is debenzylated by dissolving in 50 ml. acetic acid, adding 0.5 g. palladium-charcoal and shaking with hydrogen for 1 hour. After filtering off the catalyst and working up the filtrate, there was obtained 1.1 g. erythro-3,3'-difluoro-4,4'-dihydroxy-α-ethyl-α'-methyl-dibenzyl.

In order to demonstrate the valuable properties of the new compound according to the present invention, a first series of experiments were carried out to compare erythro-3,3'-difluoro-4,4'-dihydroxy-α-ethyl-α'-methyl-dibenzyl (Bx 341) with diethylstilboestrol, which is the best commercially available compound with a similar type of activity. The test compounds were administered orally, by means of a stomach tube, using isopropyl myristate as vehicle. The test animals used were male rats. The following Tables 1 to 3 summarise the results obtained. Table 1 shows the comparative activity of erythro-3,3'-difluoro-4,4'-dihydroxy-α-ethyl-α'-methyl-dibenzyl and diethylstilboestrol on the mean organ weights of rats during treatment and during recovery (i.e. after cessation of treatment). Table 2 shows a haematological comparison between the two test compounds during treatment therewith and Table 3 shows a haematological comparison between the two test compounds during recovery after treatment with the test compounds.

TABLE 1

Comparative Activity of erythro-3,3-difluoro-4,4'-dihydroxy-α-ethyl-α'-methyl-dibenzyl and diethylstilboestrol in Male Rats (mean organ weights)

Vehicle control  B = diethylstilboestrol  C = erythro-3,3'-difluoro-4,4'-dihydroxy-α-ethyl-α'-methyl-dibenzyl 50 g.

| | ← Treatment → | | | | | | | | |
|---|---|---|---|---|---|---|---|---|---|
| | 10 days | | | 3 weeks | | | 6 weeks | | |
| Group | A | B | C | A | B | C | A | B | C |
| Testes (g) | 2.9 ±0.08 | 2.7 ±0.11 | 2.4 ±0.16 | 3.25 ±0.08 | 1.65 ±0.18 | 2.5 ±0.24 | 3.4 ±0.11 | 1.2 ±0.29 | 2.66 ±0.16 |
| Prostrate (mg) | 220.4 ±21.42 | 129.4 ±19.3 | 81.6 ±15.83 | 359 ±31.24 | 78.5 ±9.82 | 133 ±18.33 | 511.0 ±36.9 | 95.0 ±10.8 | 130.5 ±2.74 |
| Seminal vesicles (mg) | 301 ±50 | 157.5 ±14.65 | 73 ±13.2 | 344 ±44.4 | 67.8 ±3.7 | 88 ±10.76 | 520 ±36.4 | 61 ±6.7 | 79.8 ±7.17 |
| Pituitary (mg) | 10.3 ±0.42 | 10.2 ±0.23 | 9.6 ±0.29 | 10.8 ±0.35 | 11.3 ±0.48 | 11.7 ±0.23 | 11.1 ±0.35 | 12.4 ±0.84 | 13.3 ±0.64 |
| Adrenals (mg) | 56.7 ±4.1 | 78.7 ±5.6 | 62.2 ±4.2 | 60.6 ±1.34 | 90.1 ±5.96 | 68.5 ±2 | 68.0 ±4.12 | 101.5 ±2.13 | 100.8 ±3.54 |
| Kidney (g) | 1.6 ±0.03 | 1.6 ±0.1 | 1.4 ±0.08 | 1.9 ±0.08 | 1.6 ±0.11 | 1.5 ±0.05 | 2.3 ±0.11 | 1.7 ±0.97 | 1.8 ±0.05 |

TABLE 1-continued

Comparative Activity of erythro-3,3-difluoro-4,4'-dihydroxy-α-ethyl-α'-methyl-dibenzyl and diethylstilboestrol in Male Rats (mean organ weights)

Vehicle control   B = diethylstilboestrol   C = erythro-3,3'-difluoro-4,4'-dihydroxy-α-ethyl-α'-methyl-dibenzyl 50 g.

| Liver (g) | 12.2 ±0.55 | 9.4 ±0.52 | 7.5 ±0.47 | 13.2 ±0.47 | 11.1 ±0.61 | 11.6 ±0.77 | 15.9 ±0.43 | 12 ±0.08 | 13.2 ±0.45 |
|---|---|---|---|---|---|---|---|---|---|
| Levator Ani (mg) | | | | | | | 66.6 ±4.57 | 14.9 ±1.16 | 23.5 ±2.42 |

|  | 8 weeks | | | ← Recovery → 12 weeks | | | 15 weeks | | |
|---|---|---|---|---|---|---|---|---|---|
| Group | A | B | C | A | B | C | A | B | C |
| Testes (g) | 3.33 ±0.13 | 2.11 ±0.31 | 3.18 ±0.14 | 3.4 ±0.15 | 3.3 ±0.19 | 3.4 ±0.08 | 3.7 ±0.18 | 3.7 ±0.23 | 3.6 ±0.17 |
| Prostate (mg) | 572 ±28.7 | 260 ±23.2 | 419 ±40.1 | 554 ±57.5 | 380 ±45 | 410 ±23.5 | 664 ±34.8 | 719 ±34.9 | 751 ±40.6 |
| Seminal vesicles (mg) | 534 ±54 | 207 ±18.4 | 314 ±30 | 435 ±30.8 | 375 ±38.5 | 345 ±25.1 | 642 ±43.6 | 540 ±12.7 | 572 ±25.8 |
| Pituitary (mg) | 11.6 ±0.47 | 12.2 ±0.64 | 13.9 ±1.03 | 12.7 ±0.79 | 10.7 ±1.04 | 11.2 ±1.22 | 12.3 ±1.29 | 13.8 ±0.08 | 13.2 ±0.38 |
| Adrenals (mg) | 63.9 ±2.8 | 66.9 ±3.6 | 76.7 ±3 | 56.4 ±3 | 62 ±7.65 | 57.9 ±5 | 61 ±4.2 | 72.8 ±7.6 | 50.2 ±2.7 |
| Kidney (g) | 2.3 ±0.08 | 1.7 ±0.11 | 2.3 ±0.08 | 2.4 ±0.11 | 2 ±0.08 | 2.1 ±0.14 | 2.5 ±0.14 | 2.5 ±0.13 | 2.5 ±0.15 |
| Liver (g) | 14.9 ±0.45 | 13.3 ±0.6 | 14.9 ±0.45 | 15.8 ±0.8 | 15.3 ±1.1 | 14.7 ±0.85 | 13.6 ±0.52 | 14.5 ±0.43 | 13.7 ±0.4 |
| Levator Ani (mg) | | | | | | | 85.6 ±4.51 | 83.6 ±5.8 | 89.6 ±4.6 |

TABLE 2

Long-term comparative study of the effect of erythro-3,3'-difluoro-4,4'-dihydroxy-α-ethyl-α'-methyl-dibenzyl and diethylstilboestrol in Male Rats
Haematology of male rats after treatment with erythro-3,3'-difluoro-4,4'-dihydroxy-α-ethyl-α'-methyl-dibenzyl and diethylstilboestrol

| Period of treatment | 10 days | | | 21 days | | | 42 days | | |
|---|---|---|---|---|---|---|---|---|---|
| Group: | control | diethyl-stilbo-estrol 50μg/day | BX 341 50μg/day | control | diethyl-stilbo-estrol 50μg/day | BX 341 50μg/day | control | diethyl-stilbo-estrol 50μg/day | BX 341 50μg/day |
| Haemoglobin:(g%) | 14.8±0.5 | 13.2±0.5 | 15.5±0.4 | 13.7±0.18 | 12.2±0.3 | 14.7±0.2 | 14.5±0.5 | 12.4±0.5 | 12.8±0.5 |
| Haematocrit:(%) | 41 ±0.7 | 39 ±1.0 | 44 ±1.0 | 41 ±1.0 | 40 ±1.0 | 42 ±1.0 | 41 ±1.0 | 37 ±1.9 | 40 ±0.9 |
| Erythrocyte count (millions) | 7.25±0.09 | 7.28±0.29 | 7.88±0.51 | 7.99±0.14 | 7.60±0.28 | 7.82±0.25 | 7.78±0.15 | 6.54±0.13 | 7.33±0.13 |
| Leucocyte count: (thousands) | 8.3 ±0.4 | 4.4 ±0.5 | 7.9 35 0.7 | 9.3 ±1.2 | 5.2 ±0.23 | 8.1 ±2.1 | 7.0 ±0.4 | 4.7 ±0.6 | 5.6 ±0.6 |
| Differential count (%): | | | | | | | | | |
| Lymphocytes | 82.6±2.15 | 78.0±3.0 | 79.6±4.8 | 87.4±2.2 | 76.1±4.0 | 78.0±5.0 | 85.6±1.8 | 83.0±2.4 | 83.2±2.9 |
| Neutrophils | 16.5±1.87 | 20.3±2.9 | 19.0±4.0 | 11.6±2.0 | 21.8±4.0 | 20.8±3.0 | 13.0±1.7 | 15.8±2.4 | 15.6±2.8 |
| Monocytes | 1.1 | 0.6 | 0.5 | 0.8 | 1.5 | 0.5 | 1.0 | 1.1 | 0.6 |
| Eosinophils | 0.3 | 0.3 | 0.8 | 0.2 | 0.5 | 0.6 | 0.3 | 0 | 0.5 |
| Basophils | 0 | 0 | 0 | 0 | 0.1 | 0 | 0 | 0 | 0 |
| Platelet count: (thousands) | 570±20 | 550±35 | 520±55 | 480±35 | 590±45 | 620±40 | 645±52 | 607±52 | 607±35 |

TABLE 3

Haematology of Male Rats after treatment with erythro-3,3'-difluoro-4,4'-dihydroxy-α-ethylα'-methyl-dibenzyl and diethylstilboestrol
RECOVERY STUDY

| Period of recovery | 2 weeks | | | 6 weeks | | | 9 weeks | | |
|---|---|---|---|---|---|---|---|---|---|
| Group | vehicle control | diethyl-stilbo-estrol 50μg/day | BX 341 50μg/day | vehicle control | diethyl-stilbo-estrol 50μg/day | BX 341 50μg/day | vehicle control | diethyl-stilbo-estrol 50μg/day | BX 341 50μg/day |
| Haemoglobin: (g%) | 14.22 | 14.16 | 13.03 | 15.4±0.52 | 17.1±0.62 | 16.7±1.08 | 16.2±0.65 | 15.3±0.59 | 16.5±0.23 |
| Haematocrit: (%) | 42 | 41 | 42 | 43 ±0.6 | 44±0.5 | 44±0.5 | 45±0.5 | 45±0.6 | 44±0.6 |
| Erythrocyte count (millions) | 7.69±0.07 | 7.24±0.19 | 7.25±0.14 | 8.21±0.13 | 7.82≈0.13 | 8.12±0.24 | 8.46±0.25 | 7.79±0.15 | 8.14±0.25 |
| Leucocyte count: (thousands) | 7.6±0.7 | 5.0±0.7 | 6.7±0.7 | 5.7±0.8 | 5.1±0.6 | 5.6±0.4 | 6.9±0.7 | 6.9±0.7 | 9.2±0.7 |
| Differential count (%): | | | | | | | | | |
| Lymphocytes | 87 | 82 | 79 | 85±1.8 | 82±1.35 | 80±2.78 | 82.7±2.6 | 79.3±3.1 | 86±1.1 |
| Neutrophils | 11 | 17 | 19 | 10.5±1.47 | 13.2±1.74 | 13.8±2.56 | 15.1±2.5 | 19.6±2.6 | 12±0.7 |
| Monocytes | 1.0 | 1.0 | 0.8 | 2.0 | 2.2 | 2.5 | 1.3 | 0.6 | 0.4 |
| Eosinophils | 0.1 | 0.1 | 0.1 | 1.3 | 1.0 | 1.1 | 0.8 | 0.3 | 0.4 |

TABLE 3-continued
Haematology of Male Rats after treatment with erythro-3,3'-difluoro-4,4'-dihydroxy-α-ethyl-α'-methyl-dibenzyl and diethylstilboestrol
RECOVERY STUDY

| Period of recovery | 2 weeks | | | 6 weeks | | | 9 weeks | | |
|---|---|---|---|---|---|---|---|---|---|
| Group | vehicle control | diethyl-stilbo-estrol 50μg/day | BX 341 50μg/day | vehicle control | diethyl-stilbo-estrol 50μg/day | BX 341 50μg/day | vehicle control | diethyl-stilbo-estrol 50μg/day | BX 341 50μg/day |
| Basophils | 0 | 0 | 0 | 0.1 | 1.0 | 0.8 | 0 | 0 | 0 |
| Platelet count: (thousands) | 716 | 680 | 714 | 671±51 | 670±27 | 765±29 | 533±17 | 620±24 | 572±16 |

Considerable growth retardation occurred in all treated animals for the first 3 weeks in the case of 50 μg. diethylstilboestrol but only for the first week in the case of 50 μg. erythro-3,3'-difluoro-4,4'-dihydroxy-α-ethyl-α'-methyl-dibenzyl.

It appears that the effect was partially drug-related, the food intake being only moderately reduced over this period of treatment.

During the following weeks of treatment and the recovery period, the growth rate seemed to follow a normal pattern, the animals reaching similar body weights by 14 - 15 weeks of the experiment.

The weight of testes were only moderately affected by 50 μg. erythro-3,3'-difluoro-4,4'-dihydroxy-α-ethyl-α'-methyl-dibenzyl and increased steadily over 6 weeks of treatment, reaching the weight of vehicle control rats after 2 weeks of recovery. However, 50 μg. diethylstilboestrol markedly reduced the weight of testes over 6 weeks of treatment. After 2 weeks of recovery, some slight improvement was obseveed and on the 6th week of recovery no apparent differences were seen in the weight of testes between individual animals within any group or between the animals treated and vehicle control groups.

The testicular function was reflected by presence of libido, potency and fertility in rats treated with 50 μg. erythro-3,3'-difluoro-4,4'-dihydroxy-α-ethyl-α'-methyl-dibenzyl and control rats over the treatment period but not in those treated with 50 μg. diethylstilboestrol. During the recovery period, testicular function returned gradually to normal in the rats treated with diethylstilboestrol.

On the other hand, there was not much difference in weight and size of prostate and seminal vesicles in all treated animals within the 6-week experiment, accessory sexual glands being almost equally reduced. After cessation of treatment, the recovery of accessory sexual glands appeared to be slower than the recovery of testes. Moderate increase in weight of prostate and seminal vesicles was observed after 2 - 6 weeks of recovery and full recovery after 9 weeks.

Erythro-3,3'-difluoro-4,4'-dihydroxy-α-ethyl-α'-methyl-dibenzyl did not produce the usual pituitary enlargement seen in rats receiving a prolonged silboestrol treatment. On the other hand, adrenal enlargement was noted in all treated animals.

During the treatment period, moderate alopecia occurred in some rats, mostly those treated with diethylstilboestrol. It was observed as a bilateral thinning of the hair-coat over the back in 2 - 3 cases treated with diethylstilboestrol, extending down the sides. The hair coat returned to normal within a few weeks of the recovery period.

The haematology results showed no apparent changes in the case of erythro-3,3'-difluoro-4,4'-dihydroxy-α-ethyl-α'-methyl-dibenzyl but some degree of reduction of the leucocyte count was observed, particularly in the animals treated with diethylstilboestrol.

Erythro-3,3'-difluoro-4,4'-dihydroxy-α-ethyl-α'-methyl-dibenzyl was found to be a more potent anti-androgen than diethylstilboestrol, weight for weight. The anti-androgenic effect was found to be of a similar order by both the oral and subcutaneous routes.

The results clearly demonstrate the ability of erythro-3,3'-difluoro-4,4'-dihydroxy-α-ethyl-α'-methyl-dibenzyl to produce predictable, temporary and fully reversible suppression of secondary sexual glands, without involving impairment of testicular function and fertility, even when the volume of ejaculate was likely to be reduced due to atrophy of the secondary sex glands.

The anti-androgenic potency was found to be at least as great as that of diethylstilboestrol, weight for weight, but in contrast to erythro-3,3'-difluoro-4,4'-dihydroxy-α-ethyl-α'-methyl-dibenzyl, diethylstilboestrol showed an anti-spermatogenic and anti-fertility activity, confirming known observations that suppression of fertility, spermatogenesis, libido and accessory sexual glands ran parallel in rodents treated with diethylstilboestrol and natural oestrogens.

Erythro-3,3'-difluoro-4,4'-dihydroxy-α-ethyl-α'-methyl-dibenzyl does not antagonise methyltestosterone induced growth of secondary sexual structures when both are administered concomitantly to castrated rats.

Thus, the anti-androgenic activity of erythro-3,3'-difluoro-4,4'-dihydroxy-α-ethyl-α'-methyl-dibenzyl is interpreted as a central inhibitory effect on the secretion of hypothalamic gonadotrophin-releasing factors and/or pituitary gonadotrophins and, in turn, suppression of androgen secretion by the testes.

The growth retardation appears to be partially drug-related, the food intake being only moderately reduced over a period of treatment, probably due to a drug-induced anorexia. Potent oestrogens are known to reduce serum growth hormone level and to affect growth rate and, consequently, they have been used for the treatment of some hyperpituitary states, including acromegaly.

Erythro-3,3'-difluoro-4,4'-dihydroxy-α-ethyl-α'-methyl-dibenzyl, at the dosage level used, did not produce the usual pituitary enlargement seen in rats receiving a prolonged diethylstilboestrol treatment.

On the other hand, adrenal enlargement was noted in all treated animals: this oestrogenic effect is mediated through the pituitary but it is not considered to be of great toxicological significance. Adrenal cortical hyperplesia may or may not be considered.

The results described above indicate endocrine control therapy with erythro-3,3'-difluoro-4,4'-dihydroxy- α-ethyl-α'-methyl-dibenzyl in prostate enlargement and in prostate diseases, and also indicate that it is superior to and safer than diethyl stilboestrol.

A comparison has also been made between erythro-3,3'-difluoro-4,4'-dihydroxy-α-ethyl-α'-methyl-dibenzyl and two closely related but known compounds, namely, 3,3'-difluoro-4,4'-dihydroxy-α,α-diethyl-dibenzyl (BX 362) and 3,3'-difluoro-4,4'-dihydroxy-α,α-dimethyl-benzyl (BX 368). The test compounds were administered daily in isopropyl myristate by means of a stomach tube for a period of 10 days. The effects on body organ weights of male rats are set out in the following Table 4:

TABLE 4

INHIBITION OF GONADOTROPHIN RELEASE IN RATS

| Compound | Rat No. | Mean Body Weight PM | Gain (g) | Dose mg/kg/day | Mean weight of (mg.) | | | | | | |
|---|---|---|---|---|---|---|---|---|---|---|---|
| | | | | | Testes | Ventral Prostate | Seminal Vesicles | Levator Ani | Adrenals | Thymus | Pituitary |
| Control | 10 | 201 | 49 | — | 2500 | 152 | 175 | 21.4 | 58 | 511 | 8.6 |
| Vehicle *) | 10 | 200 | 54 | — | 2570 | 153 | 174 | 21.7 | 53 | 582 | 7.6 |
| BX 341 | 10 | 165 | 25 | 1.6 | 1400 | 32 | 35 | 11.5 | 60 | 371 | 9.0 |
| BX 362 | 10 | 150 | 3 | 1.6 | 1740 | 46.6 | 46 | 7.2 | 61 | 287 | 8.5 |
| BX 368 | 10 | 171 | 18 | 1.6 | 1900 | 61 | 46.2 | 12.3 | 59 | 408 | 8.9 |

*) Isopropyl myristate 0.2 ml./rat/day

These results support the findings in the first series of experiments and also show that erythro-3,3'-difluoro-4,4'-dihydroxy-α-ethyl-α'-methyl-dibenzyl has a better effect in reducing the weight of the prostate than the two known compounds (BX 362 and BX 368).

In a further series of experiments, the oestrogenic activities were determined of erythro-3,3'-difluoro-4,4'-dihydroxy-α-ethyl-α'-methyl-dibenzyl, BX 362, BX 368 and diethylstilboestrol from a measurement of the uterine weight response on female mice (10 mice per group) and from the uterine weight ratio, this latter ratio being calculated as follows:

(uterine weight (mg.)/body weight (g)) × 100

Here again, the test compounds were administered subcutaneously in isopropyl myristate for 3 days. The results obtained are set out in the following Tables 5 and 6:

TABLE 5

MEAN UTERINE WEIGHT (mg.)

| Compound | daily dose μg/kg. | |
|---|---|---|
| | 2.5 | 5.0 |
| Diethylstilboestrol | 43.5 | 55.2 |
| BX 362 | 32.6 | 40.5 |
| BX 368 | 17.4 | 18.5 |
| BX 341 | 13.5 | 20.5 |

TABLE 6

UTERINE RATIO

| Compound | daily dose g/kg. | |
|---|---|---|
| | 2.5 | 5.0 |
| Diethylstilboestrol | 382 | 587 |
| BX 362 | 357 | 408 |
| BX 368 | 176 | 201 |
| BX 341 | 118 | 169 |

The results given in Tables 5 and 6 show that the oestrogenic activity of erythro-3,3'-difluoro-4,4'-dihydroxy-α-ethyl-α'-methyl-dibenzyl is less than that of diethylstilboestrol, 3,3'-difluoro-4,4'-dihydroxy-α,α'-diethyl-dibenzyl (BX 362) and 3,3'-difluoro-4,4'-dihydroxy-α,α'-dimethyl-dibenzyl (BX 368), which is, of course, desirable for the administration of erythro-3,3'-difluoro-4,4'-dihydroxy-α-ethyl-α'-methyl-dibenzyl to males for the treatment of diseases of the prostate.

The present invention also includes within its scope pharmaceutical compositions containing the new compound. These pharmaceutical compositions can be administered orally or parenterally in admixture with a solid or liquid pharmaceutical carrier.

Solid compositions for oral administration include compressed tablets, pills, dispersible powders and granules. In such solid compositions, the active compound according to the present invention is admixed with at least one inert diluent, such as tribasic calcium phosphate ($Ca_3(PO_4)_2$), starch, lactose, gelatine, acacia, sucrose, stearic acid, talc, algenic acid or sodium alginate. The compositions may also comprise, as is normal practice, additional substances other than inert diluents, for example, lubricating agents, such as magnesium stearate, as well as sweetening or flavouring agents.

The percentage of active ingredient in the compositions of the present invention may be varied, it being necessary that it should constitute a proportion such that a suitable dosage for the desired therapeutic effect shall be obtained. In general, the preparations of the present invention should be administered in an effective dose from about 0.00001 mg. to 1 mg. of active substance per kg. of body weight per day.

The following Example illustrates a pharmaceutical composition according to the present invention:

EXAMPLE 4

Ingredients for the preparation of 100,000 tablets, each containing 20μg. of active material:

| | |
|---|---|
| erythro-3,3'-difluoro-4,4'-dihydroxy-α-ethyl-α'-methyl-dibenzyl | 2.00 g. |
| lactose | 3900.00 g. |
| starch | 998.00 g. |
| magnesium stearate | 100.00 g. |

The lactose was first milled to a fine powder and sieved into the bowl of a planetary or trough mixer. The dibenzyl derivative was dissolved in 100 ml. ethanol and mixed with the lactose, mixing being continued for 30 minutes. The starch was sieved and sufficient pure water added thereto to give a 10% by weight starch paste. After subtracting the amount needed for granulation, the remainder of the starch paste was introduced into the mixing vessel and mixing continued for 15 minutes. Granulation was then carried out with the calculated quantity of starch paste at ambient temperature and mixing continued for a further 15 minutes.

The granulate obtained was sieved through a 16 mesh screen, laid out in a thin layer and dried for 12 hours with forced ventilation at a temperature of 35° – 40° C. The dried granulate was then sieved through a 20 mesh screen and returned to the planetary or trough mixer. The magnesium stearate was then sieved through a 60 mesh screen, added to the granulate and mixing continued for 30 minutes. The granulate was then compressed into 50 mg. tablets, each of which contained 20 g. of the dibenzyl derivative.

The above tablets are for administration to human males for the treatment of hypertrophied conditions of the prostate.

What we claim is:

1. 3,3'-Difluoro-4,4'-dihydroxy-α-ethyl-α'-methyl-dibenzyl.

2. A pharmaceutical composition for the treatment of hypertrophied conditions of the prostate, said composition suitable for oral administration which comprises an effective amount of 3,3'-difluoro-4,4'-dihydroxy-α-ethyl-α'-methyl-dibenzyl, in admixture with a solid or liquid pharmaceutical diluent or carrier.

3. A treatment of treating a hypertrophied condition of the prostate in animals which comprises orally administering to an animal suffering from such condition, an effective amount of 3,3'-difluoro-4,4'-dihydroxy-α-ethyl-α'-methyl-dibenzyl.

* * * * *